United States Patent
Donati et al.

(10) Patent No.: US 7,799,338 B2
(45) Date of Patent: Sep. 21, 2010

(54) PLASTER FOR TOPICAL USE CONTAINING HEPARIN AND DICLOFENAC

(75) Inventors: Elisabetta Donati, Cavallasca (IT); Irina Rapaport, Rovio (CH)

(73) Assignee: Altergon SpA, Lugano (CH)

( * ) Notice: Subject to any disclaimer, the term of this patent is extended or adjusted under 35 U.S.C. 154(b) by 1503 days.

(21) Appl. No.: 10/957,031

(22) Filed: Oct. 4, 2004

(65) Prior Publication Data

US 2005/0048101 A1    Mar. 3, 2005

Related U.S. Application Data

(60) Continuation of application No. 10/448,492, filed on May 29, 2003, now abandoned, which is a division of application No. 09/549,254, filed on Apr. 14, 2000, now Pat. No. 6,592,891.

(51) Int. Cl.
- *A61K 9/70* (2006.01)
- *A61K 31/727* (2006.01)
- *A61K 31/136* (2006.01)
- *A61P 17/02* (2006.01)

(52) U.S. Cl. ............... 424/448; 514/56; 514/658
(58) Field of Classification Search ............ None
See application file for complete search history.

(56) References Cited

U.S. PATENT DOCUMENTS

| | | | | |
|---|---|---|---|---|
| 4,879,282 A | * | 11/1989 | Saliba, Jr. ............ | 514/56 |
| 5,217,954 A | * | 6/1993 | Foster et al. ........... | 514/12 |
| 5,260,066 A | * | 11/1993 | Wood et al. ........... | 424/447 |
| 5,668,119 A | * | 9/1997 | Medenica ............ | 514/56 |
| 6,166,084 A | * | 12/2000 | Bloor ................... | 514/613 |

FOREIGN PATENT DOCUMENTS

WO    WO 97/42944    *    5/1997

OTHER PUBLICATIONS

Belcaro et al. Angiology. 2005; 56 (6): 707-713, abstract only.*

* cited by examiner

*Primary Examiner*—Shanon A Foley
(74) *Attorney, Agent, or Firm*—Hedman & Costigan, P.C; James V. Costigan

(57) ABSTRACT

Plaster for topical use having an analgesic activity and at the same time being able to re-absorb haematomas, comprising:
a substrate layer;
an adhesive layer in the form of a hydrogel matrix containing a pharmaceutically acceptable diclofenac salt, heparin or a heparinoid;
a protective film which can be removed at the moment of use.

15 Claims, No Drawings

PLASTER FOR TOPICAL USE CONTAINING HEPARIN AND DICLOFENAC

This is a continuation of Ser. No. 10/448,492, filed May 29, 2003 now abandoned which is a division of Ser. No. 09/549,254, filed Apr. 14, 2000 now U.S. Pat. No. 6,592,891 which claims priority from Italian Application Ser. No. MI1999A000834, filed Apr. 21, 1999.

SCOPE OF INVENTION

Plaster for topical use having an analgesic activity and being able to re-absorb haematomas, containing diclofenac in association with heparin or a heparinoid.

STATE OF THE ART

Known and available on the market are creams for topical use with a base of heparinoids, possibly in association with hyaluronidase, for re-absorption of haematomas and ecchymoses.

Though remarkably effective, these creams involve a number of drawbacks. In fact, they do not present a more specific analgesic activity, which would be particularly necessary in the case of serious ecchymoses.

In addition, the creams, the application of which involves first spreading the cream, and subsequently rubbing or gentle massaging on the area affected, do not enable uniform dosing of the active principle from one application to the next. In addition, with this type of formulation it is not possible to control in any way the release of active principle; consequently, these formulations must be applied on the area affected at least twice a day, with considerable inconvenience, in that they necessarily leave greasy residue on the skin.

In the European Patent Application EP-A-621263, a plaster is described containing as active principle only diclofenac in the form of a pharmaceutically acceptable salt with an N-hydroxyalkyl alicyclic amine.

This type of plaster represents an alternative system to oral administration of diclofenac, and administration which, as is known, presents considerable undesirable effects at the gastric level.

SUMMARY OF INVENTION

The applicant has now discovered a plaster containing heparin or heparinoids in association with diclofenac or one of its salts that is pharmaceutically acceptable for topical use, which does not present the drawbacks of the cream compositions that are known for the same type of use.

This plaster in particular comprises:
a) a substrate layer;
b) an adhesive layer in the form of a hydrogel matrix in which the above-mentioned active principles are dispersed;
c) a protective film which can be removed at the moment of use.

DETAILED DESCRIPTION OF INVENTION

In the plaster according to the present invention, diclofenac is generally present in the form of a pharmaceutically acceptable salt, and preferably it is a salt with a heterocyclic amine of general formula:

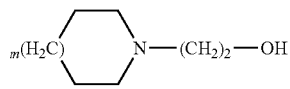

where m is 0 or 1.

According to a particularly preferred embodiment, the heterocyclic amine is N-hydroxyethyl pyrrolidine (epolamine).

The diclofenac salt is contained in the plaster according to the present invention in concentrations generally ranging from 0.1 to 5 wt %, preferably in concentrations of between 0.3 and 3 wt % with respect to the total weight of the composition used for the preparation of the hydrogel matrix.

According to a particularly preferred embodiment, the concentration of the diclofenac salt is 1.3 wt % with respect to the total weight of the composition used for the preparation of the hydrogel matrix.

When the plaster according to the present invention contains a heparinoid, the latter preferably presents a molecular weight of between 5,000 and 30,000 DA.

The heparin or heparinoid is present in concentrations such that its total quantity in the plaster is between 0.05 and 1%, which corresponds respectively to a concentration range of between 1,400 and 28,000 IU/plaster (100-2,000 IU/g matrix).

According to a particularly preferred embodiment, heparin is contained in concentrations such that the corresponding content is 5600 IU per plaster.

It is advisable that the composition used for preparing the hydrogel matrix should present pH values of between 7.2 and 9, preferably of between 7.5 and 8.5. At pH values lower than 7.2, the diclofenac crystals that are insoluble in water precipitate; values higher than 9 may cause irritation of the skin. To adjust the pH of the hydrogel composition, any organic or inorganic acid, or any organic or inorganic base may be used, without any particular limitation. The concentration of the above-mentioned acid or base is not critical either and may vary according to the pH value that the hydrogel composition reaches.

In addition to the aforementioned active principles, the hydrogel matrix further contains thickening agents, wetting agents, fillers, preservatives, cross-linking agents, surfactants, stabilizers, and the like.

Preferably, the composition used for the preparation of the hydrogel matrix contains as thickening agents the following: polyacrylic acid, sodium polyacrylate, sodium carboxymethyl cellulose, polyvinyl alcohol, polyvinyl pyrrolidone, gelatine or corresponding mixtures. The concentration of the above additives is generally between 3 and 30 wt %, preferably between 5 and 20 wt %. If the concentration is lower than 3 wt %, the viscosity of the composition is too low, so that the composition comes out of the plaster and remains on the skin once the plaster is applied; on the other hand, if the concentration is too high, it is not very workable. According to a particularly preferred embodiment, the thickening agents are a mixture consisting of the following: gelatine, polyvinyl pyrrolidone, sodium polyacrylate, and sodium carboxymethyl cellulose in a total concentration of 9 wt % with respect to the total weight of the hydrogel matrix.

The hydrogel matrix of the plaster according to the present invention preferably comprises at least one wetting agent chosen from among glycerol, propylene glycol, polyethylene glycol, 1,3-butanediol, and an aqueous solution of D-sorbitol, preferably in a concentration of 70 wt %.

The concentration of the said wetting agents in the composition used for the preparation of the hydrogel matrix according to the present invention is between 5 and 70 wt %, preferably between 10 and 60 wt % with respect to the total weight of the composition used for the preparation of the hydrogel matrix.

If the quantity of wetting agent is lower than 5%, the wetting effect is not sufficient and the composition dries quickly; if, instead, the quantity of wetting agent is higher than 70%, mixing of the components is difficult.

The cross-linking agent is preferably an aluminum or calcium compound present in the composition used for the preparation of the hydrogel matrix in a concentration of between 0.01 and 3.0 wt %. If the quantity of this additive is lower than 0.01 wt %, cross-linking is insufficient, so that the resistance to heat of the hydrogel matrix is reduced; consequently, two drawbacks may occur, either during storage or during application: during storage, the composition is too fluid and comes out of the plaster in the sterile container in the sterile container of the latter; when the plaster is applied, the composition leaves a residue on the skin. When the concentration of the cross-linking agent is higher than 3%, the rate of cross-linking is too high and consequently the viscosity of the composition used for the preparation of hydrogel matrix increases, so that the corresponding workability decreases.

As a filler, one of the following, for instance, may be used: kaolin, titanium dioxide, bentonite, or mixtures of the said compounds.

As a preservative, the hydrogel matrix that is the subject of the present invention may contain either preservatives of a conventional type, such as the esters of para-alkyloxy benzoic acid, for example Nipagin and Nipasol, or sorbic acid. The hydrogel matrix may possibly contain a surfactant, such as a polyoxyethylene sorbitan ester (Tween 80) and a stabilizer, such as sodium ethylenediamine tetraacetate.

As far as the substrate layer is concerned, any material usually employed for this purpose may be used, such as fabric, non-woven fabric, paper, plastic film and corresponding laminates.

As regards the removable protective film, this may be of a conventional type, for instance, siliconized paper, or may be made of a plastic material, such as polyethylene, polyethylene terephthalate, or polyvinyl chloride.

The present plaster is prepared according to conventional methods which, in particular, envisage the following fundamental stages:
mixing of the various components of the composition used for the preparation of the hydrogel matrix,
co-extrusion of the hydrogel matrix between the substrate layer and the removable protective film.

The mixing phase is in particular conducted in the following stages:
1-A) mixing of one part of water with the filler and with part both of the cross-linking agent and of the thickening agent;
1-B) subsequent addition to the mixture obtained in stage (1-A) of further thickening agents;
1-C) addition to the mixture obtained in stage (1-B) of preservatives, a stabilizer, a pH adjuster, as well as of the remaining part of the cross-linking agent and thickening and wetting agents;
1-D) addition to the mixture obtained in stage (1-C) of the pharmaceutically acceptable diclofenac salt;
1-E) addition to the mixture obtained in stage (1-D) of the heparin or heparinoid.

To provide a non-limiting illustration, an example is given of preparation of the hydrogel matrix used as adhesive layer of the plaster according to the present invention.

| COMPONENTS | % (p/p) |
| --- | --- |
| DIEP | 1.3 |
| Sodium heparin 198 IU/mg | 0.202 (5600 IU) per plaster |
| Gelatine | 2.0 |
| Polyvinyl pyrrolidone | 2.0 |
| Nipagin | 0.1 |

-continued

| COMPONENTS | % (p/p) |
| --- | --- |
| Nipasol | 0.05 |
| Propylene glycol | 3.0 |
| Tween 80 | 0.2 |
| Kaolin | 3.0 |
| Titanium dioxide | 0.5 |
| Sorbitol | 40.0 |
| EDTA Na | 0.12 |
| tartaric acid | 0.5 |
| Aluminium glycinate | 0.3 |
| Sodium polyacrylate | 4.0 |
| Sodium carboxymethyl cellulose | 3.0 |
| Butylene glycol | 10.0 |
| Water | 29.73 |

One part of water, kaolin, titanium dioxide and 70% sorbitol is added; to this is added, in the form of an aqueous solution, one half of the quantity of dihydroxy aluminium glycinate, sodium polyacrylate, sodium carboxymethyl cellulose, and 1,3-butanediol. Everything is mixed by stirring.

To the mixture thus obtained is added an aqueous mixture of gelatine and polyvinyl pyrrolidone, an aqueous solution containing Nipagin, Nipasol, NaEDTA, tartaric acid, and finally an aqueous solution consisting of the remaining part of aluminium glycinate, 1,3-butanediol, sodium carboxymethyl cellulose and sodium polyacrylate, and subsequently the product is mixed under stirring.

To the mixture thus obtained, finally the active principles are added; first, a solution is added of the diclofenac salt with N-hydroxyethyl pyrrolidine (DIEP), and finally a heparin aqueous solution, to obtain the composition given in the table above, which is subsequently extruded.

The invention claimed is:

1. A therapeutic method for an analgesic and re-absorption treatment of hematomas which consists of a topical application of a bandage comprising: a) a substrate layer; b) an adhesive layer in the form of a polymeric hydrogel matrix comprising a pharmaceutically acceptable diclofenac salt and heparin or a heparinoid, at least one thickening agent, at least one wetting agent, at least one cross-linking agent, and c) a protective film which can be removed at the moment of use, wherein said hydrogel matrix further comprises a surfactant consisting of a polyoxyethylene sorbitan ester and a stabilizer consisting of sodium ethylenediamine tetraacetate.

2. The method according to claim 1, characterized in that the diclofenac salt is in the form of a salt with an alicyclic amine of general formula

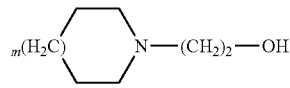

:in which m is 0 or 1.

3. The method according to claim 1 characterized in that the diclofenac salt is the salt of N-hydroxyethyl pyrrolidine.

4. The method according to claim 1, characterized in that the concentration of the diclofenac salt is between 0.1 and 5 wt % with respect to the hydrogel matrix.

5. The method according to claim 4, characterized in that the concentration of the diclofenac salt is between 0.3 and 3 wt % with respect to the hydrogel matrix.

6. The method according to claim 1 in which the concentration of heparin or heparinoid is between 0.05 and 1 wt % with respect to the hydrogel matrix.

7. The method according to claim 1 characterized in that the pH of the composition used for the preparation of the hydrogel matrix is between 7.2 and 9.

8. The method according claim 7, characterized in that the pH is between 7.5 and 8.5.

9. The method according to claim 1 in which the concentration of polyoxyethylene sorbitan ester is 0.2 wt % with respect to the hydrogel matrix.

10. The method according to claim 1, wherein the concentration of sodium ethylene diamine tetraacetate is 0.12% by weight with respect to the hydrogel matrix.

11. The method according to claim 1, characterized in that the concentration of the diclofenac salt is between 0.1 and 5 wt % with respect to the hydrogel matrix.

12. The method according to claim 1, characterized in that the concentration of the diclofenac salt is between 0.3 and 3 wt % with respect to the hydrogel matrix.

13. The method according to claim 2 in which the concentration of heparin or heparinoid is between 0.05 and 1 wt % with respect to the hydrogel matrix.

14. The method according to claim 2 characterized in that the pH of the composition used for the preparation of the hydrogel matrix is between 7.2 and 9.

15. The method according to claim 2 in which the concentration of polyoxyethylene sorbitan ester is 0.2 wt % with respect to the hydrogel matrix.

* * * * *